United States Patent
Weiss et al.

(10) Patent No.: US 6,512,239 B1
(45) Date of Patent: Jan. 28, 2003

(54) STEREO VISION INSPECTION SYSTEM FOR TRANSPARENT MEDIA

(75) Inventors: Adam Weiss, Pickering (CA); Alexandre Obotnine, Willowdale (CA)

(73) Assignee: Photon Dynamics Canada Inc., Markham (CA)

( * ) Notice: Subject to any disclaimer, the term of this patent is extended or adjusted under 35 U.S.C. 154(b) by 195 days.

(21) Appl. No.: 09/604,532

(22) Filed: Jun. 27, 2000

(51) Int. Cl.$^7$ .............................................. G01N 21/86
(52) U.S. Cl. ................. 250/559.4; 356/239.4
(58) Field of Search .............. 250/559.4; 356/239.5, 356/239.7, 239.4

(56) References Cited

U.S. PATENT DOCUMENTS

| | | | |
|---|---|---|---|
| 3,737,665 A | | 6/1973 | Nagae |
| 4,492,477 A | | 1/1985 | Leser |
| 4,583,854 A | | 4/1986 | Lozar |
| 4,641,966 A | | 2/1987 | Lemmers et al. |
| 4,691,231 A | * | 9/1987 | Fitzmorris et al. .......... 358/106 |
| 5,459,330 A | | 10/1995 | Venaille et al. |
| 5,969,810 A | * | 10/1999 | Nicks et al. ............. 356/239.4 |
| 6,011,620 A | | 1/2000 | Sites et al. |
| 6,088,092 A | * | 6/2000 | Chen et al. ............... 356/237.2 |
| 6,104,482 A | * | 8/2000 | Brower et al. ........... 356/239.4 |
| 6,275,287 B1 | * | 8/2001 | Watanabe ................. 356/239.4 |
| 6,396,579 B1 | * | 5/2002 | Hayamizu et al. ....... 356/239.7 |

FOREIGN PATENT DOCUMENTS

| | | |
|---|---|---|
| CA | 2252308 | 10/1998 |
| DE | 3926349 A1 | 8/1989 |
| DE | 41 39 094 | 11/1991 |
| DE | 198 09 505 | 3/1998 |
| EP | 0 317 638 | 5/1988 |
| EP | 0 317 638 | 8/1989 |
| EP | 0 559 916 | 9/1992 |
| GB | 1 526 930 | 12/1974 |
| WO | WO 96/05503 | 2/1996 |
| WO | WO 00/26647 | 5/2000 |

OTHER PUBLICATIONS

Patent Abstracts of Japan, vol. 1997, No. 04, Apr. 30, 1997, for: JP 08 327561 A, Dec. 13, 1996.
Patent Abstracts of Japan, vol. 016, No. 468, Sep. 29, 1992, for: JP 04 168251, Jun. 16, 1992.
Patent Abstracts of Japan, vol. 1996, No. 11, Nov. 29, 1996, for: JP 08 193955, Jul. 30, 1996.
International Search Report for: PCT/CA99/00953, completed: Dec. 20, 1999.

* cited by examiner

*Primary Examiner*—Robert H. Kim
*Assistant Examiner*—Irakli Kiknadze
(74) *Attorney, Agent, or Firm*—Merchant & Gould P.C.

(57) ABSTRACT

Apparatus and a method for the detection and identification of defects in a transparent medium, especially light diverting and transparent defects with optical properties. The apparatus comprises an extended source of illumination, first and second optical recording devices, and a means to pass the transparent medium between the extended source of illumination and the first and second optical recording devices. The first and second optical recording devices are disposed to record images at opposed acute angles from a common location on the transparent medium. The second optical recording device has two sources of laser illumination attached thereto, which are directed at the common location in a spaced apart relationship such that scattered of laser light from surfaces of the transparent medium is recorded by the first optical recording device.

31 Claims, 6 Drawing Sheets

STEREO VISION INSPECTION SYSTEM FOR TRANSPARENT MEDIA

FIELD OF THE INVENTION

The present invention relates to a non-contact inspection system for detection and identification of defects, especially light diverting and transparent defects with optical properties, in transparent media. The system is intended to operate on a continuous production line at line speed, for the detection and location of a variety of types of defects, including bubbles, scratches, cracks, inclusions and other defects in a variety of transparent media including flat and curved glass and plastic articles. In particular, the invention is intended to identify the location of the defect within the thickness of the transparent medium, using stereo vision.

BACKGROUND OF THE INVENTION

In processes for manufacture of transparent media, it is necessary to be able to inspect the transparent media for defects. Such defects may be in the form of scratches, bubbles, chips, blemishes and a wide variety of other defects. However, the mere detection of defects is insufficient in that the manufacturer of the transparent media needs to know whether the defects are insignificant e.g. minor in nature and thus acceptable to the customer, or a major flaw such that the transparent media would not conform to specifications established by the customer.

It is possible to use human visual inspection of transparent media and to identify those articles of transparent media that have defects. In addition, using visual inspection, it is possible to identify the location and possibly the type of defect. However, human visual inspection is not acceptable because of the time and cost involved in conducting a visual inspection, and the limitations of such a method. It would be preferable to be able to conduct the inspection on-line in the production process, at production speeds, so that defects could be rapidly identified and communicated to production personnel and/or the articles of transparent media with the defects could be readily and quickly separated from articles meeting quality specifications in an effective manner.

Methods have been developed for the inspection of sheets of glass using optical techniques that involve use of lasers. While lasers can be very effective in the detection of defects in flat or essentially flat sheets of glass, imaging optics for laser light require a small f-stop i.e. a large aperture and consequently the depth of field is small. This limits the usefulness of laser light, especially in circumstances where the glass or article has curvature. One example of such a curved article is the face plate of a cathode ray tube (CRT), which requires good optical properties. Focusing on the surface of a curved article to detect defects is difficult if the depth of field of the imaging optics is small.

SUMMARY OF THE INVENTION

Apparatus and a method have now been found for detection, identification and location of defects, especially light diverting with optical properties, in a transparent medium using stereo vision techniques.

Accordingly, one aspect of the present invention provides apparatus for the detection and measurement of light diverting and transparent defects with optical properties in a transparent medium, comprising:

a) an extended source of illumination:
b) a first optical recording device;
c) a second optical recording device:
d) means to pass said transparent medium between said extended source of illumination and said first and second optical recording devices,
said first and second optical recording devices being disposed to record images at opposed acute angles from a common location on the transparent medium,
said second optical recording device having two sources of laser illumination attached thereto, said sources of laser illumination being directed at said common location in a spaced apart relationship such that laser light scattered by surfaces of the transparent medium is recorded by the first optical recording device.

In a preferred embodiment of the present invention, said first and second optical recording devices are adapted to be moved from a first location to a second location on the transparent medium.

A further aspect of the present invention provides a method for the detection and measurement of light diverting and transparent defects with optical properties in a transparent medium, in apparatus comprising:

a) an extended source of illumination:
b) a first optical recording device;
c) a second optical recording device:
d) means to pass said transparent medium between said extended source of illumination and said first and second optical recording devices,
said first and second optical recording devices being disposed to record images at opposed acute angles from a common location on the transparent medium,
said second optical recording device having two sources of laser illumination attached thereto, said sources of laser illumination being directed at said common location in a spaced apart relationship such that laser light scattered by the transparent medium is recorded by the first optical recording device;
said method comprising passing an article of a transparent medium between said extended source of illumination and said optical recording devices,
illuminating said transparent medium with said extended source of illumination and said laser illumination,
recording images of said transparent medium with each of said optical recording devices, including recording laser illumination scattered by opposed upper and lower surfaces of the transparent medium at said common location, and
determining the location of said defect within the transparent medium.

BRIEF DESCRIPTION OF THE DRAWINGS

The present invention is illustrated by the embodiments shown in the drawings, in which.

DETAILED DESCRIPTION OF THE INVENTION

The present invention is directed to inspection of a variety of types of transparent media for optical defects. Examples of the types of transparent media include both glass and plastics. The glass may be, for instance, flat sheets of glass, e.g. float glass and tempered glass, formed sheets of glass e.g. curved glass, laminated glass e.g. windshields and moulded glass e.g. cathode ray tube (CRT) and lens blanks. The plastic may be moulded plastic e.g. opthalmic lens blanks and other curved structures as well as curved and flat transparent sheets of plastics. The invention may also be used for the inspection of other curved or flat transparent media.

Techniques for the manufacture of glass are known. For example, glass may be converted to a molten state and then cast into a mould or onto molten tin metal so that glass with a smooth surface may be obtained. Nonetheless, the glass that has been cast may be subject to a number of defects, including the presence of bubbles, dirt, stones, tin-drip distortion and other defects. Some such defects might arise from raw materials fed to the process while other defects will arise from processing problems, including incorrect temperature or other process parameters and aging of apparatus, especially of kilns or other apparatus used in the heating of the glass.

Subsequent to the casting and any cutting of the glass, the glass is transferred to a manufacturer of glass articles for a particular end-use. In the automobile industry, for instance, the glass articles could be the windows of the vehicle, in which event the manufacturer will shape the glass to a particular size and configuration, prepare ground edges to the glass, cut holes in the glass in locations as required, imprint logos or other writing in the glass and otherwise process the cut glass to a predetermined set of specifications. Despite care in operation of the process, the various steps can result in the formation of chips, cracks, scratches, and other defects that might render the glass unacceptable to a customer. The manufacturer must be able to detect the defects, and separate sheets of glass conforming to specification from those that do not. In other embodiments, the glass is flat sheet intended for end-uses other than the automobile industry.

Examples of some of the defects that may be present in a sheet of glass include bubbles i.e. inclusion of gas in the glass in a generally spherical shape, blisters i.e. elongated bubbles, seeds i.e. minute bubbles, dirt, lint, shell chips i.e. small pieces of glass broken away from the main body of the glass, stones, strands i.e. very fine, string-like pieces of foreign matter embedded in the glass or laminates thereof, vents i.e. small cracks usually appearing at the corners of cut glass, pits or digs i.e. small hollows and other defects.

Alternatively, the glass may be curved or formed glass. Such curved glass might be intended for the automobile industry, but it could be intended for other end-uses. For instance, the glass could be the face plate of a cathode ray tube (CRT) for a television or a computer. Such glass is normally cast into a mould. All such glass must meet the particular specifications for the manufacturer of articles from the glass, and ultimately meet the requirements of the end-user e.g. the purchaser of the television or computer. Examples of defects that may occur in curved glass e.g. CRT glass, include scratches, pits i.e. open blisters, elongated blisters, cords or viscous strings, cold glass, stones and thermal pressure defects.

It is to be understood that in some instances the glass may be in the form of a laminated or tempered glass or other glass, to give it strength, shatter resistance or other properties. The processes used to form such glass may add to the potential defects in the sheet of glass.

Although the sheet or article has been described above with respect to glass, the sheet or article may be formed from a transparent plastic, or other transparent media rather than glass. The defects in the transparent plastic or other transparent media might be the same as found in glass or different e.g. defects arising from the manufacture of the plastic composition that is used and the subsequent processing into an article. The latter defects include gel, dirt, bubbles, stress lines, surface phenomena and the like.

Figure 1:
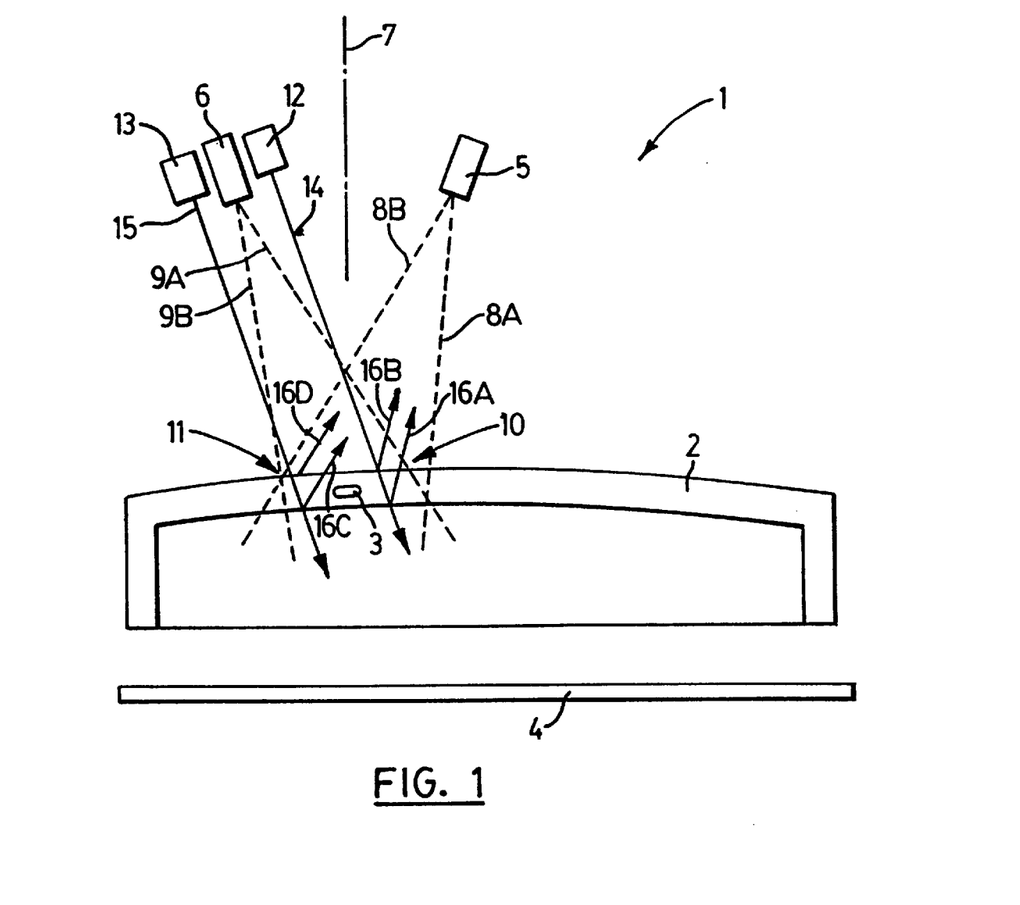
FIG. 1 is a schematic representation of apparatus of the present invention.

FIG. 1 shows a schematic representation of apparatus 1 of the present invention used in stereo vision inspection of a transparent medium 2. Transparent medium 2 is transported through apparatus 1 on rollers that are not shown in FIG. 1. A defect 3 in the form of a bubble, is shown in transparent medium 2.

Apparatus 1 has illuminator 4, which is a light source with distributed illumination. Illuminator is shown as located beneath transparent medium 2. Optical recording devices 5 and 6 are shown on the opposed side of transparent medium 2 from illuminator 4. Optical recording devices 5 and 6 are time delay integration (TDI) devices, and may be referred to herein as cameras. Optical recording devices 5 and 6 are at an acute angle to axis 7, being on opposite sides of axis 7. The field of view of optical recording device 5 is indicated by lines 8A and 8B, and similarly the field of view of optical recording device 6 is indicated by lines 9A and 9B. Thus, optical recording devices 5 and 6 have a common viewing area on transparent medium 2 between points 10 and 11.

Optical recording device 6 has first laser 12 and second laser 13 attached thereto. First laser 12 emits laser light beam 14 and second laser emits laser light beam 15. Laser light beams 14 and 15 are directed at transport medium 2, and intersect transparent medium 2 in a spaced apart relationship in the common viewing area of optical recording devices 5 and 6 i.e. between pints 10 and 11.

In operation, transparent medium 2 is passed on the roller (not shown) between illuminator 4 and optical recording devices 5 and 6, and is lit by light from illuminator 4. Optical recording devices 5 and 6 record images from transparent medium 2, including the presence of defects 3 when it is in the area viewed by the optical recording devices. In addition, optical recording device 5 records the laser light 14 and 15 scattered from the upper and lower surfaces of transparent medium 2, as indicated by interceptions 16A–16D.

The position of optical recording devices 4 and 6, as are the locations of laser light 14 and 15. Thus, the location of interceptions 16A–16D with the surfaces of transparent medium 2 can be determined, which provides information on the thickness of transparent medium 2. In addition, images of defect 3 are recorded by optical recording device 5 and by optical recording device 6. Thus, the position of defect 3 may be determined within the thickens of transparent medium 2.

Figure 2:
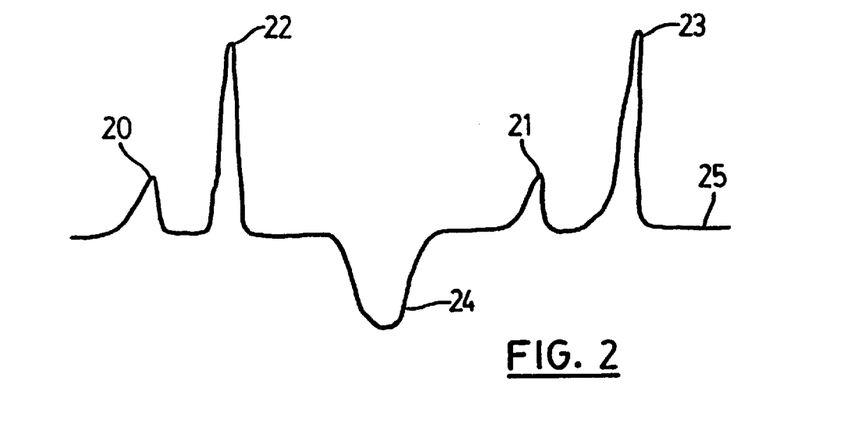
FIG. 2 is a schematic representation of images recorded using the apparatus of FIG. 1.

A representation of images received by optical recording device 5 is shown in FIG. 2 Images 22 and 23 represent the scattering from the lower surface of transparent medium 2, being interceptions 16C and 16A of FIG. 1 Images 20 and 21 represent scattering from the upper surface of transparent medium 2, being interceptions 16D and 16B of FIG. 1 Images 22 and 23 are larger than images 20 and 21 because the upper surface is a polished exterior i.e. almost non-scattering, surface of transparent medium 2, whereas the lower surface is an interior surface slightly diffusing surface. Image 24 represents defect 3, and is obtained as a loss of light recorded by optical recording device 5 in comparison with the base line 25 of light transmitted through transparent medium 2 from illuminator 4.

Figure 3:
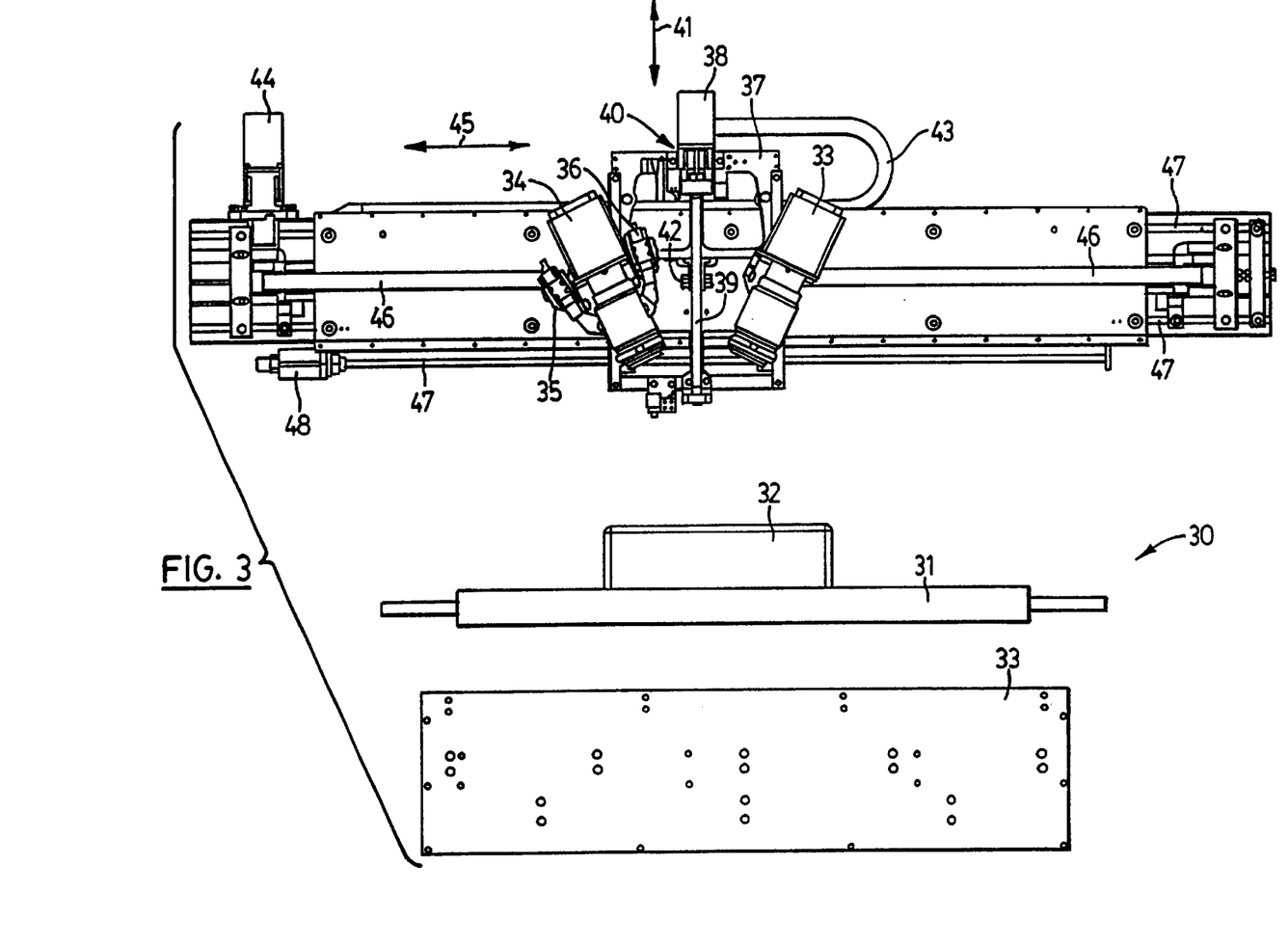
FIG. 3 is a schematic representation of an end view of an embodiment of apparatus of the present invention.

FIG. 3 shows an end view of an embodiment of apparatus of the present invention. Apparatus 30 has a plurality of rollers, 31, of which only one is shown. Rollers 31 transport transparent medium 32, which is shown in the form of a face plate for a cathode ray tube (CRT). Illuminator 33 is located beneath rollers 31, and is adapted to shine light up through rollers 31 and transparent medium 32.

Optical recording devices 33 and 34, in the form of cameras, are located on measurement head 37. Optical recording device 34 has lasers 35 and 36 attached thereto. Optical recording devices 33 and 34 are up opposed acute angles to the axis therebetween.

Measurement head 37 has motor 38, which is attached to lead screw 39 that passes through coupler 40. Motor 38 is adapted to move measurement head 37 in a vertical direction, as indicated by arrow 41. Rotary motion of lead screw 39 through roller nut 42 effects vertical movement of measurement head 37. Motor 44 is adapted to move measurement head 37 in a horizontal direction, as indicated by arrow 45. Motor 44 effects movement of measurement head 37 by means of belt 46, and guide rails 47.

Movement of measurement head 37 in a vertical direction is primarily intended to permit focusing of the cameras on the transparent medium that is being subjected to inspection. In particular, the height of the cameras may be adjust to accommodate transparent media of different heights being transported on rollers 31. Movement of measurement head 37 in a horizontal direction is intended to permit traversing of the cameras across the width of the transparent medium 32 to a location of a defect. In this embodiment, it is intended that the stereo vision system described herein would be used in association with another inspection system that would identify the presence and location of a defect in transparent medium 32. The stereo vision system would then be used by movement of measurement head 37 so that optical recording devices 33 and 34 were directed at the location of the defect in transparent medium 32. In this manner, the nature of the defect, and in particular the determination of whether the defect was a surface defect or a defect within the matrix of the transparent medium could be determined.

Cable 43 is used in the control of the positions of optical recording devices 33 and 34, by means of motor 38.

Absolute displacement transducer 48 provides feedback to the electronics used in the control of the position of head 37.

Figure 4:
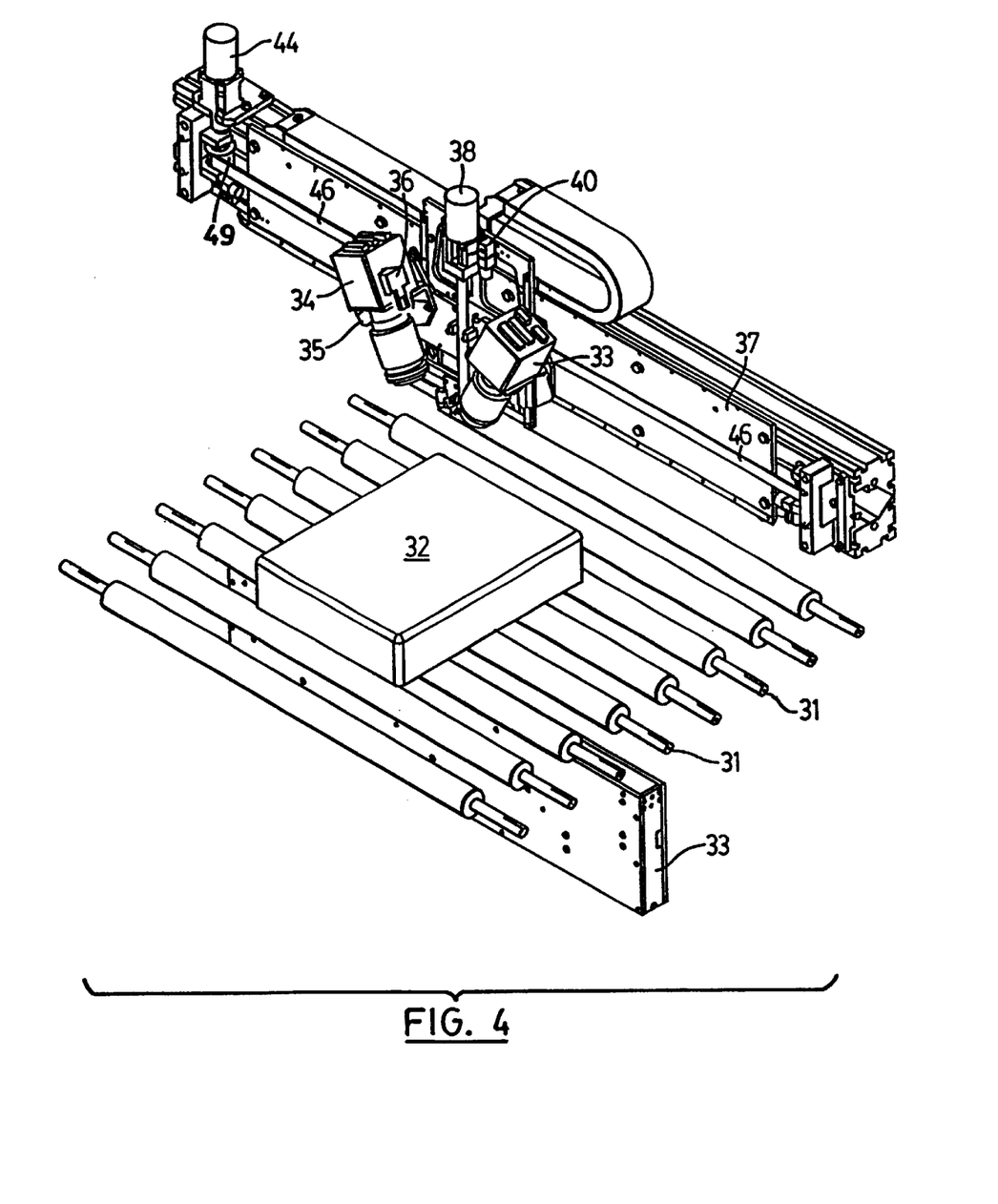
FIG. 4 is a schematic representation of a perspective view of the apparatus of FIG. 3.

FIG. 4 shows a perspective view of the apparatus of FIG. 3. Transparent medium 32 is transported on a plurality of rollers 31, to pass over illuminator 33. Measurement head 37 may be moved in a vertical direction using motor 38 or in a horizontal direction using motor 44, as described previously. Belt 46 is moved on rotation of cog 48.

Figure 5:
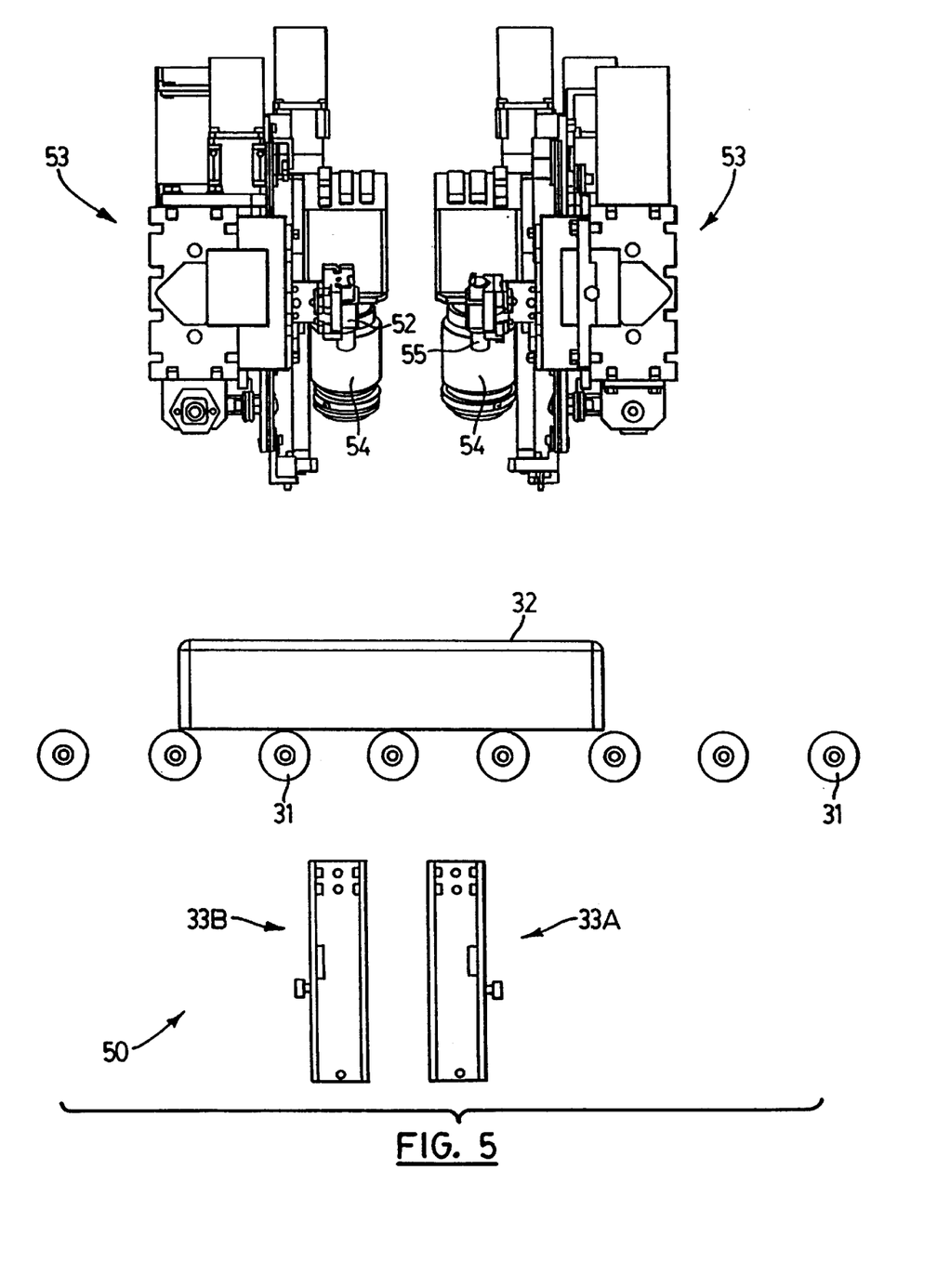
FIG. 5 is a schematic representation of a side view of an embodiment of apparatus of the invention, with dual sets of optical recording devices.

FIG. 5 shows a side view of a stereo view system of the present invention, in which two or dual stereo view units are used in the inspection. In apparatus 50, illuminators 33A and 33B are located beneath the plurality of rollers 31 that transport transparent medium 32 through apparatus 50. Transparent medium 32 is shown in the form of the face plate of a cathode ray tube.

An optical recording device 51 with lasers 52 (only one shown in FIG. 5) is attached to first measurement head 53. It is understood that a second optical recording device as described previously would be associated with optical recording device 51 but is not seen in FIG. 5. A measurement head has been described previously.

An optical recording device 54 with lasers 55 (only one shown) is attached to second measurement head 56. Second measurement head 56 would also have a second optical recording device, not shown.

As described previously, each of measurement heads 53 and 56 are capable of being moved in a horizontal direction and a vertical direction. The horizontal direction is transverse to the direction of movement of transparent medium 32. Movement of each measurement head 53 and 56 is normally independent of the other. For example, when a transport medium with known defects is passed along rollers 31, one measurement head may be directed to move so as to observe a first defect, and the other measurement head may be directed to move to observe a second defect. However, both measurement heads could be directed to the same defect e.g. to obtain higher resolution of the defect. Use of two measurement heads is a preferred embodiment of the invention, as the inspection system is more versatile and can review multiple defects at line speed.

The stereo view inspection system described herein may be used in association with a one or both of viewing area inspection system and a dark view inspection system. The full combination of systems is shown in FIG. 6.

Figure 6:
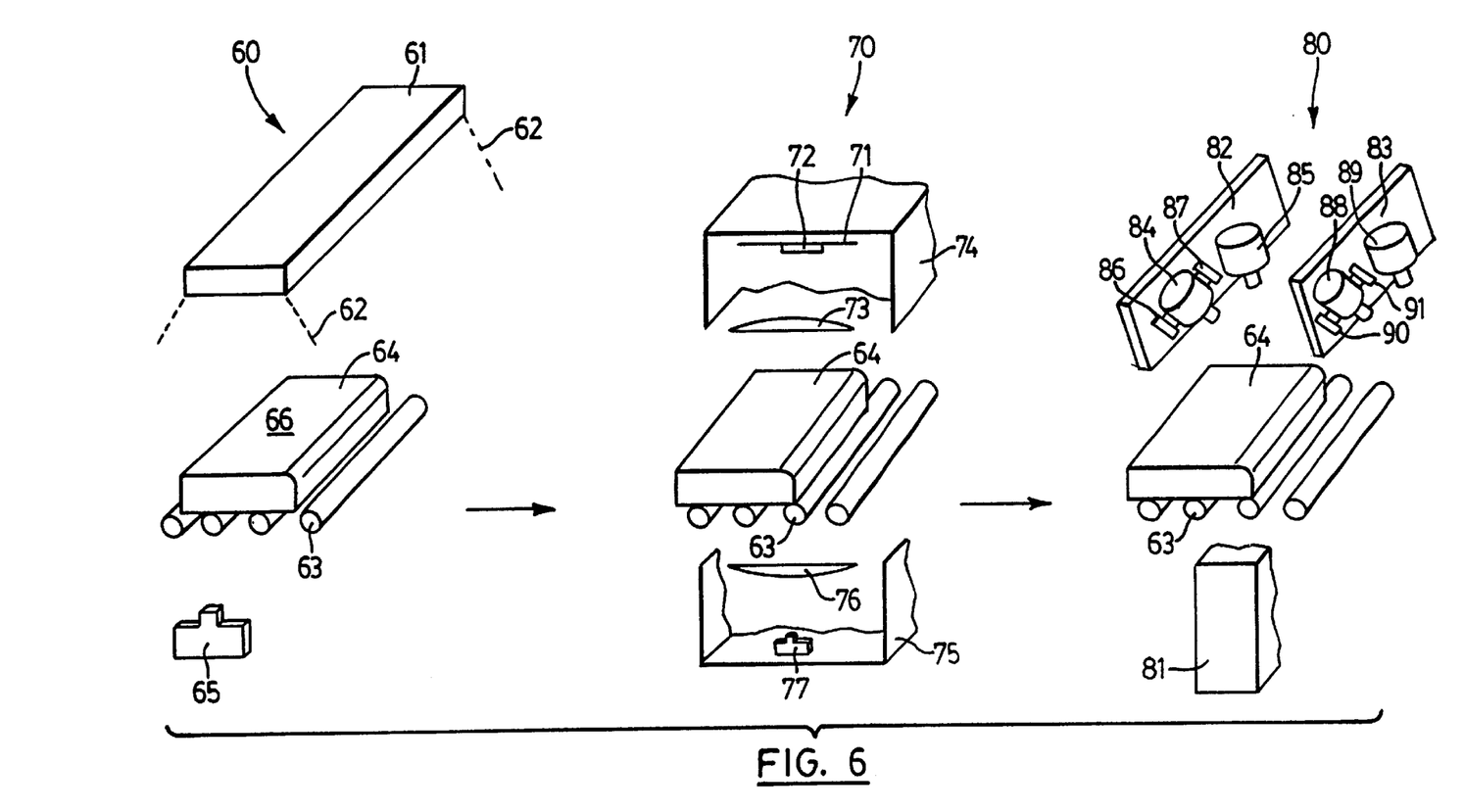
FIG. 6 is a schematic representation of a combination of apparatus for detection of defects.

FIG. 6 shows a viewing area inspection system, generally indicated by 60, in-line with a dark view inspection system, generally indicated by 70, and a stereo vision inspection system, generally indicated by 80.

Viewing area inspection system 60 has an illuminator 61, which preferably provides distributed illumination as indicated by 62. A series of rollers 63 are provided to move a transparent medium 64 through the viewing area inspection system. Transparent medium 64 is shown in the form of a face plate for a cathode ray tube (CRT) which is one preferred form of the transparent medium to be inspected. An optical recording device e.g. a camera, 65 is located beneath rollers 63 to record images from transparent medium 64. Lenses may be provided to assist in the focusing and directing of light to optical recording device 65. Optical recording device 65 would be focused at the upper surface 66 of transparent medium 64.

FIG. 6 also shows dark view inspection system 70 which is preferably located in series with viewing area inspection system 60, and most preferably utilizes the same series of rollers 63 as viewing area inspection system 60. Similarly, stereo view inspection system 80 is preferably located in-line and in series with both viewing area inspection system 60 and dark view inspection system 70, and most preferably uses the same set of rollers 63. Continuous transportation of a transparent medium 64 is important so that the transparent medium 64 is in the same orientation in both inspection systems. As discussed herein, the preferred method of operation is to pass the transparent medium through the systems in sequence, and use computer software to locate and identify defects.

Dark view inspection system 70 has light source 71 that provides distributed illumination, except at aperture stop 72. Light source 71, aperture stop 72 and first lens 73 are located in upper housing 74, which is preferably coated with a black light-absorbing coating, to reduce or eliminate reflections. Lower housing 75 has second lens 76 and optical recording device 77. Lower housing 75 is also preferably coated with a black light-absorbing coating.

It is to be understood that the stereo vision inspection system described herein may be used with one or both of a viewing area inspection system and a dark view inspection system. If all three systems are used in sequence, the viewing area inspection system should be located first in the sequence of systems, primarily to permit the location of defects to be identified. The dark view inspection system would normally be located second in the sequence of systems, primarily because it can identify and locate light diverting and transparent defects with optical properties. The stereo vision inspection system would normally be located third in the sequence of systems, primarily because it can locate the depth of the defect in a transparent medium.

Stereo view inspection system 80 has been described above. Illuminator 81 provides distributed illumination, and is located below rollers 63. Two measurement heads 82 and 83 are located above transparent medium 64. Measurement head 82 has optical recording devices 84 and 85, with optical recording device 84 having lasers 86 and 87. Optical recording devices 84 and 85 are disposed at acute angles to the axis therebetween, and focused at a common location. Laser light from lasers 86 and 87 is viewed and recorded. Similarly, measurement head 83 has optical recording devices 88 and 89, with optical recording device 88 having lasers 90 and 91.

In operation, a transparent medium 64 is passed into viewing area inspection system 60. An image of the transparent medium 64 is recorded by optical recording device 65. The images recorded by optical recording device 65 will include the edges of transparent medium, which is then used to locate the position of any defects observed and inspected in subsequent steps in the process.

Maintaining the transparent medium 64 on the same rollers and in the same orientation permits combination of the images obtained by optical recording devices 65 and 77, to provide a composite image of transparent medium 64. In addition, the composite image is used to dispatch the measurement heads 82 and 83 to inspect defects.

In the dark view imaging system, which is the subject of co-pending U.S. patent application No. (unknown) (client reference 8930-58) filed (unknown) and incorporated herein by reference, light is passed from light source 71 through first lens 73, transparent medium 64 and second lens 76 to the plane of optical recording device 77. However, the arrangement of lenses and the presence of aperture stop 72 on light source 71 causes the light to not be recorded by optical recording device 77. Instead, optical recording device 77 records an image of aperture stop 72 i.e. effectively an absence of light. However, if a light diverting and transparent defect with optical properties is present in transparent medium 64, the light will be diverted by the defect into the region recorded by optical recording device 77. Such an image can be tracked as transparent medium 64 moves on rollers 63.

Figure 7:
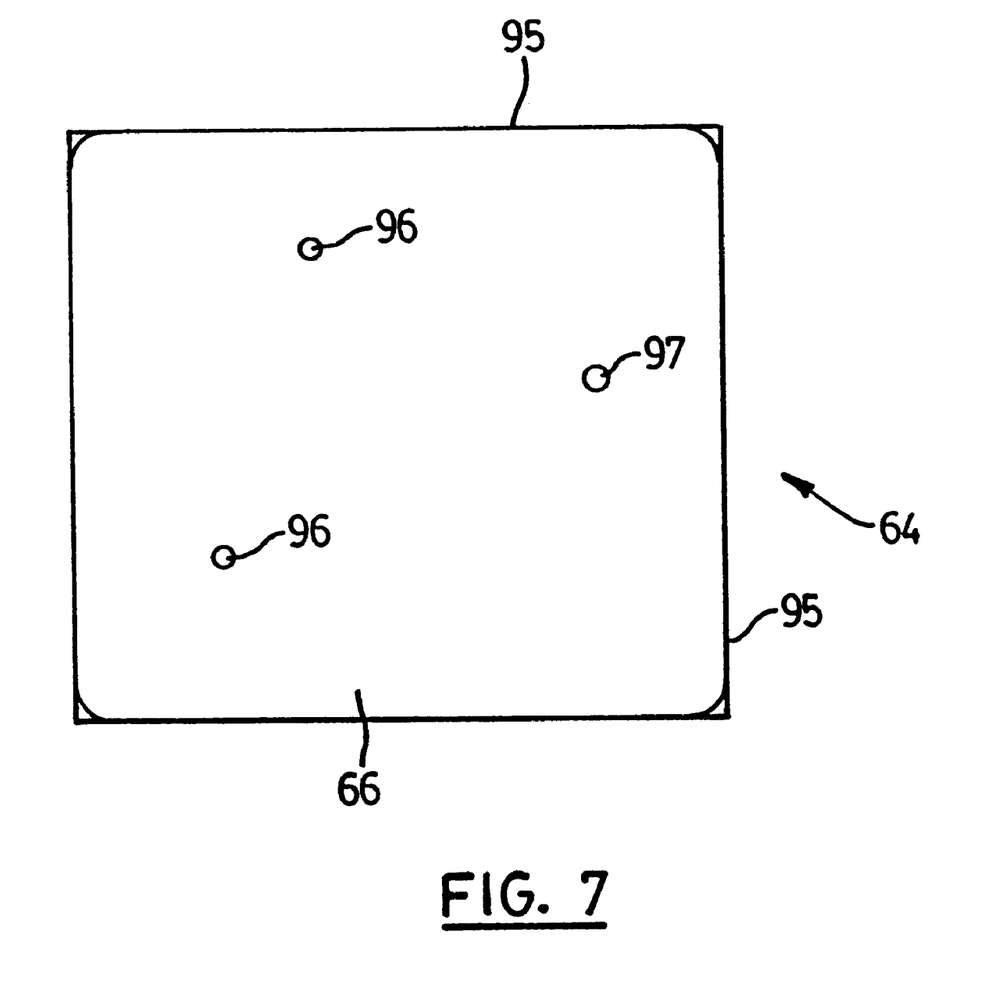
FIG. 7 is a schematic representation of an image obtained in the apparatus of FIG. 6.

The combination of the viewing area inspection system and dark view inspection system permits computer software to determine the location of defects. An example of a composite image is shown in FIG. 7. The image is of upper surface 66 of transparent medium 64, with edges 95 of transparent medium 64 being shown. Edges 95 provide the reference points for locating of defects 96 and 97. Defect 96 is a light diverting and transparent defect with optical properties that would be observed by the dark view optical recording device 77. Such a defect might additionally be observed by the viewing area optical recording device 65. Defect 97 is an opaque defect e.g. a piece of solid matter such as a piece of sand, which would be observed and located by both optical recording device 65 and optical recording device 77.

A composite image such as shown in FIG. 7 is used to direct the movement of the measurement heads of the stereo vision inspection system. The coordinates of defects 95 and 96 are known, and the speed of travel of transparent medium 64 is also known. Thus, arrival of a defect in the viewing region of the stereo view inspection system can be predicted, especially using computer software. The measurement heads of the stereo view inspection system can thus be moved backwards and forwards and/or up and down to record images of the defects as required.

The nature and characteristics of the images obtained by the optical recording devices, including whether defects are observed by one or both optical recording devices, provides information on the type and source of the defects. Such information assists in determining whether the transparent medium meets specifications, and assists in identifying the source and causes of the defects. The stereo vision inspection system provides further information, especially on the depth of the defect and the thickness of the transparent medium. It may be possible to polish or grind the surface of the transparent medium to remove a defect and obtain a sample of transparent medium that meets production specifications.

All optical recording devices would be connected to a computer having software to record and analyze the images received, and with information on the rate of movement of the transparent medium, to coordinate and combine the image. Analysis of images has been discussed above.

A variety of viewing area inspection systems may be used. For instance, if the transparent medium was a flat sheet of transparent medium, the viewing area inspection system could be the inspection system of Adam Weiss and Alexandre Obotnine disclosed in Canadian patent application No. 2,252,308 filed Oct. 30, 1998, which utilizes lasers instead of distributed illumination.

The present invention provides a glass inspection system that is capable of automation, and which utilizes optics and a computer vision-based system. The system utilizes a combination of broad illumination techniques, rather than a laser system. The system may be used with a variety of transparent media, including glass and plastics.

In preferred embodiments of the invention, the inspection system provides an advanced image analysis with exceptional detection limits, down to 3 $\mu$m, as well as the capability to detect and differentiate a wide variety of defects including scratches, bubbles, chips, blemishes and other defects, and identifies the location, type and magnitude of the defects in the transparent medium. The system is capable of being operated at high-speeds e.g. at lines speeds of up to 0.3 m/sec, or higher. In addition, the dark view method of the present invention permits use of a TDI camera, which substantially increases sensitivity and reduces the power requirements for the light source. Thus, the inspection system may be used in-line in many manufacturing processes.

The software used in the system may be featured with a menu-based graphical user interface for ease of use, pass/fail specification changes and new model set ups, as well as automatic change over and calibration of the system.

In a preferred embodiment, a standard user interface screen with a defect map is used, having coloured icons that represent various types of defects. For examples, circles may be used to represent bubbles, squares to represent chips, triangles to represent scratches and so on. The icons may be made to appear at the actual x,y co-ordinates where the defects are located in the sheet of glass. In addition, the icons may be colour coded to represent the size of the defects e.g. the icons could be green to represent a very small defect, yellow to represent a medium defect and red to represent a large defect or reject. Moreover, software may be provided where the user can "click" on any icon to provide characteristics of the defect, including type, size and location. 3-D visualization and mapping of the defects is also possible. Removable surface contaminants such as dust and water, may or may not be reported by the system, depending on the particular application of the system.

It is to be understood that electronic hardware would be interfaced with the detection system. This hardware would provide for control of the detection system, collection of pixel data from the collection system, compression of the data by relaying for further processing only data that is related to areas of interest in the glass sheet, and for pre-processing of pixel data by applying multilevel thresholds and marking transitions between different levels of intensities. A dedicated Peripheral Process Board (PPB) may be used to further process the data by means of software. The processed data may then be transmitted to a gauge host computer for the purpose of visualization and control, as discussed herein.

The detection system may be set to recognize a threshold of illumination that indicates the presence of defects in the transparent medium. The threshold may be set at levels that represent defects that are unacceptable in the transparent medium being tested, but not recognize defects that would pass specification. All other information e.g. noise or changes in light intensity that do not cause the light intensity to pass through a threshold could be ignored. The transitions that pass through the threshold may be presented on a computer display tube.

The position of the transparent medium within the apparatus is not important, provided that it is located within the width of the light beam. Moreover, the method of the present invention is capable of being used with curved articles of the transparent medium, including CRT face plates. Computer software may be used to more precisely show the location of defects in curved transparent media.

The apparatus is preferably operated with an air pressure slightly above atmospheric pressure so that there is a gentle flow of air outwards from the apparatus, to prevent dust particles being brought into the apparatus. In addition, the air circulated within the apparatus may be passed through at least one HEPA filter, as well as electronic filters, with the air being exchanged frequently e.g. every five minutes. It is important to eliminate dust particles, or at least maintain the dust particles at a minimum, as the lenses are normally within the depth of field of the camera, and dust particles on the lenses will be recognized and interpreted as defects.

Time delayed integration techniques may be used in the detection and analysis of the images that are formed and detected.

The present invention provides a versatile apparatus and method for inspection of transparent media, and which is capable of simultaneously identifying a wide variety of defects by type, magnitude and location, in a manner that not only permits identification of transparent media that does not meet product specifications but also assists in identifying the causes of the defects.

What is claimed is:

1. Apparatus for the detection and identification of defects in a transparent medium, comprising:
   a) an extended source of illumination:
   b) a first optical recording device;
   c) a second optical recording device:
   d) means to pass said transparent medium between said extended source of illumination and said first and second optical recording devices,
      said first and second optical recording devices being disposed to record images at opposed acute angles from a common location on the transparent medium,
      said second optical recording device having two sources of laser illumination attached thereto, said sources of laser illumination being directed at said common location in a spaced apart relationship such that laser light scattered by surfaces of the transparent medium is recorded by the first optical recording device.

2. The apparatus of claim 1 in which said first and second optical recording devices are adapted to be moved from a first location to a second location on the transparent medium.

3. The apparatus of claim 2 in which the location of the defect may be determined.

4. The apparatus of claim 2 in which the first and second optical recording devices are adapted to be moved towards and away from said transparent medium.

5. The apparatus of claim 4 in which the first and second optical recording devices are attached to a moveable measurement head.

6. The apparatus of claim 5 in which there are at least two moveable measurement heads, each moveable measurement head having a first and second optical recording device and each moveable measurement head being moveable independent of each other moveable measurement head.

7. The apparatus of claim 5 in which the system additionally comprises software to determine the location, type and magnitude of light diverting and transparent defects with optical properties in the sheet of transparent medium.

8. The apparatus of claim 7 in which the system additionally has means to record the location, type and magnitude of light diverting and transparent defects with optical properties in the transparent medium, optionally including a display or a defect map, especially a defect map displayed on a screen.

9. The apparatus of claim 1 in which the light source is a distributed light source.

10. The apparatus of claim 1 in which the transparent medium is glass.

11. The apparatus of claim 1 in which the transparent medium is plastic.

12. The apparatus of claim 1 in which detection and identification includes a measurement of size.

13. A method for the detection and measurement of light diverting and transparent defects with optical properties in a transparent medium, in apparatus comprising:
   a) an extended source of illumination:
   b) a first optical recording device;
   c) a second optical recording device:
   d) means to pass said transparent medium between said extended source of illumination and said first and second optical recording devices,
      said first and second optical recording devices being disposed to record images at opposed acute angles from a common location on the transparent medium,
      said second optical recording device having two sources of laser illumination attached thereto, said sources of laser illumination being directed at said common location in a spaced apart relationship such that laser light scattered by the transparent medium is recorded by the first optical recording device;

said method comprising passing an article of a transparent medium between said extended source of illumination and said optical recording devices, illuminating said transparent medium with said extended source of illumination and said laser illumination, recording images of said transparent medium with each of said optical recording devices, including recording laser illumination scattered by opposed upper and lower surfaces of the transparent medium at said common location, and determining the location of said defect within the transparent medium.

14. The method of claim 13 in which the defects are light diverting and transparent defects with optical properties.

15. The method of claim 14 which detection and identification includes a measurement of size.

16. The method of claim 13 in which said recording of diverted light is analysed using computer software.

17. The method of claim 12 in which said software determines the location, type and magnitude of light diverting and transparent defects with optical properties in the transparent medium.

18. The method of claim 16 in which defects having a size down to 3 microns are detected.

19. The method of claim 16 in which the transparent medium is flat glass.

20. The method of claim 16 which the transparent medium is curved glass.

21. The method of claim 16 which the transparent medium is formed glass.

22. The method of claims 16 which the transparent medium is the face plate of a cathode ray tube.

23. Apparatus for the detection and identification of defects in a transparent medium, comprising:

a) light sources of extended length and width, each light source providing a column of light;

b) means to pass said transparent medium through said columns of light;

c) a first optical recording device associated with a first light source and a second optical recording device associated with a second light source, said second light source having an aperture stop and a lens system to form a column of light from said light source and to focus said light at a plane, a lens system focusing an image of said aperture stop at said plane, said second optical recording device being located at said image; and d) a third light source associated with two optical recording devices, one of said optical recording devices having two sources of laser light, said optical recording devices being adapted to obtain a stereo image, said stereo images including scattered of laser light.

24. The apparatus of claim 23 in which the system additionally comprises software to determine the location, type and magnitude of light diverting and transparent defects with optical properties in the sheet of transparent medium.

25. The apparatus of claim 24 in which the system additionally has means to record the location, type and magnitude of defects in the transparent medium, optionally including a display or a defect map.

26. The apparatus of claim 25 in which a defect map is displayed on a screen.

27. The apparatus of claim 24 in which the apparatus is adapted to identify light diverting and transparent defects with optical properties in the transparent medium.

28. A method for the detection and identification of defects in a transparent medium, comprising:

a) passing said transparent medium through first and second light sources of extended length and width, each light source providing a column of light;

b) focusing the column of light from the first light source at a first optical recording device and focusing the column of light from the second light source at a second optical recording device;

c) recording images of said transparent medium at said first and second optical recording devices; and d) combining said images for detection and identification of the defects.

29. The method of claim 28 in which the defects include light diverting and transparent defects with optical properties.

30. The method of claim 29 in which the image are analyzed using computer software.

31. The method of claim 30 in which said software determines the location, type and magnitude of light diverting and transparent defects with optical properties in the transparent medium.

* * * * *